United States Patent [19]

Tamblyn

[11] Patent Number: 4,933,433

[45] Date of Patent: Jun. 12, 1990

[54] RECOMBINANT INTERLEUKIN-2 COMPOSITION AND PROCESS FOR MAKING IT

[75] Inventor: Toby M. Tamblyn, Newark, Del.

[73] Assignee: E. I. Du Pont de Nemours and Company, Wilmington, Del.

[21] Appl. No.: 825,133

[22] Filed: Jan. 31, 1986

[51] Int. Cl.$^5$ .................... C07K 15/00; A61K 37/02
[52] U.S. Cl. .................. 530/351; 530/412; 530/417; 514/970; 514/2; 514/8; 424/85.1; 424/85.2
[58] Field of Search ............ 530/351, 412, 417; 514/2, 8; 424/85.1, 85.2

[56] References Cited

U.S. PATENT DOCUMENTS

| | | | |
|---|---|---|---|
| 4,401,756 | 8/1983 | Gillis | 435/68 |
| 4,490,289 | 12/1984 | Stern | 260/112 R |
| 4,518,584 | 5/1985 | Mark et al. | 424/85 |
| 4,530,787 | 7/1985 | Shaked et al. | 260/112 R |
| 4,569,790 | 2/1986 | Koths et al. | 530/351 |
| 4,604,377 | 8/1986 | Fernandes et al. | 424/85.2 |
| 4,623,717 | 11/1986 | Fernandes et al. | 530/380 |
| 4,645,830 | 2/1987 | Yasushi et al. | 530/351 |
| 4,714,611 | 12/1987 | Yasaburgo et al. | 435/68 |
| 4,738,927 | 4/1988 | Taniguchi et al. | 530/351 |

FOREIGN PATENT DOCUMENTS

| | | |
|---|---|---|
| 0035204 | 9/1981 | European Pat. Off. . |
| 0092163 | 10/1983 | European Pat. Off. . |
| 0136090 | 3/1985 | European Pat. Off. . |
| 133767 | 6/1985 | European Pat. Off. . |
| 0145390 | 6/1985 | European Pat. Off. . |
| 8504328 | 10/1985 | PCT Int'l Appl. . |

OTHER PUBLICATIONS

Urdal et al., *Journal of Chromatography*, 296, 171–179 (1984).
Taniguchi et al., *Nature*, 302, 305 (1983).
Rosenberg et al., *Science*, 223, 1412–1415 (1984).
Gekko et al., *Biochemistry*, 20, 4677–4686 (1981).
Liang et al., *Biochem. J.*, 229, 429–439 (1985).
Mita et al., *Biochemical and Biophysical Research Communications*, 117, 114–121 (1983).
Mier and Gallo (1982), *J. Immunol.*, 128:1122–1127.
Hanson et al. (1983), *J. Immunol.* 130:216–221.
Pichyangkul & Khan (1986), *Proceedings of the Society for Experimental Biology and Medicine*, 183:231–236.
Katre et al., *PNAS* 84, 1987, pp. 1487–1491.
Gearing et al., *Lymphokine Res.* 5, 1986, pp. S19–S21.

*Primary Examiner*—Garnette D. Draper

[57] ABSTRACT

There are disclosed a recombinant interleukin-2 composition consisting essentially of water, recombinant interleukin-2, and optionally a polyol, said composition having a specific activity of at least about 120,000 units/mg and a process for preparing it by heating a suspension of the interleukin-2 at a specified temperature.

18 Claims, No Drawings

RECOMBINANT INTERLEUKIN-2 COMPOSITION AND PROCESS FOR MAKING IT

BACKGROUND OF THE INVENTION

1. Field of the Invention

This invention relates to a recombinant interleukin-2 composition and a process for preparing it.

2. References

Interleukin-2 (IL-2) is a soluble protein which is capable of modulating lymphocyte reactivity and promoting the long-term in vitro culture of antigen-specific effector T-lymphocytes and, in the past, has been produced by stimulating mouse, rat or human lymphocyte cells with a mitogen. Human IL-2 consists of a 133 amino acid polypeptide containing a single intramolecular disulfide bridge.

U.S. Pat. No. 4,401,756, issued to Gillis on August 30, 1983, discloses a process for preparing IL-2 from malignant cells by culturing human leukemia or lymphoma cells in a serum containing medium supplemented with various additives. The culture is stimulated by an optimum concentration of T-cell mitogen to produce a supernate which contains IL-2. After a period of time, the supernate is collected and processed to purify the IL-2. The patent discloses that a cell line designated Jurkat-FHCRC is a preferred source of leukemic human T-cells.

U.S. Pat. No. 4,490,289, issued to Stern on December 25, 1985, discloses a process for purifying human IL-2 derived from induced human malignant cells. The IL-2 is purified to homogeneity by using multiple steps of reverse phase high performance liquid chromatography. The patent discloses that the purified IL-2 exhibits potent activity promoting the long-term in vitro culture of antigen-specific effector T-lymphocytes and in modulating lymphocyte activity. The Jurkat-FHCRC leukemic human T cell line is said to be a preferred cell line and the resulting purified material is disclosed in one example as having an activity of 205,000 units/ml and in another example of 983,040 units/ml. The patent mentions a prior art preparation of IL-2 from normal lymphocytes which was unstable even at −70° C. and required bovine serum albumin (BSA) or polyethylene glycol to retain activity. One unit of activity is defined in the patent as the number of microliters present in a T cell culture well which induced 50% of maximal thymidine incorporation.

Urdal, et al., *Journal of Chromatography*, 296, 171–179 (1984), disclose the purification of human IL-2 (Jurkat) on a $C_8$ reverse-phase column in pyridine-acetate-propanol followed by chromatography on a $C_{18}$ reverse-phase column in trifluoroacetic acid-acetonitrile.

Taniguchi, et al., *Nature*, 302, 305 (1983), disclose the isolation of a human IL-2 complementary DNA clone from the Jurkat cell line and the determination of its nucleotide sequence.

Rosenberg, et al., *Science*, 223, 1412–1415 (1984), disclose the isolation of the gene for interleukin-2 from the Jurkat cell line and from normal peripheral blood lymphocytes, insertion of the gene into *Escherichia coli*, and expression of the gene by the resulting transformed microorganism. The IL-2 was purified to apparent homogeneity. The authors reported that no functional differences between native and recombinant IL-2 molecules were detected.

European patent application No. 84304992.5, European publication No. 0 133 767 A2, discloses that gamma interferon obtainable from the human leukocytes, which is unstable even during lyophilization and storage in solid state, can be stabilized by addition of albumin and/or a sugar. Usable sugars are said to include monosaccharides, disaccharides, sugar alcohols and mixtures thereof. Specifically mentioned are compounds such as glucose, mannose, galactose, fructose, sucrose, maltose, lactose, mannitol and xylitol. The publication also discloses that a stable, lyophilized gamma interferon composition is prepared by lyophilizing its aqueous solution containing this stabilizer without lowering its activity.

Gekko, et al., *Biochemistry* 20, 4677–4686 (1981) discuss a thermodynamic and kinetic study of protein stabilization by glycerol. The particular proteins involved were chymotrypsinogen and ribonuclease.

When recombinant IL-2 (rIL-2) is produced from transformed *E. coli*, the rIL-2 is recovered and purified in a post-fermentation process which involves sonicating the cell paste, extracting the useful protein, purifying the extracted rIL-2 by use of reverse phase high performance liquid chromatography (HPLC), and resuspending the resulting purified rIL-2 in water often with a carrier such as human serum albumin. If the rIL-2 is not going to be used immediately, generally it is lyophilized after HPLC purification and resuspended when needed. The specific activity of this resuspended rIL-2 composition is typically below about 50,000 units/mg of protein, which is about 16.7% of that of pure human Jurkat IL-2, but may be as high as about 90,000 units/mg.

When a protein such as IL-2 is to be used for therapeutic purposes, it is desirable that the specific activity be as high as possible, thereby minimizing concern about possible detrimental effects of the inactive protein. Moreover, recently there has been considerable public concern about using any biological products having a component derived from human blood. This concern has most recently been centered on plasma-derived factor VIII and natural human growth hormone but could include components such as human serum albumin. Thus, a rIL-2 composition with high specific activity and lacking any carrier derived from human blood is highly desirable.

SUMMARY OF THE INVENTION

The present invention provides a recombinant human IL-2 composition consisting essentially of water, recombinant human IL-2 and, optionally, a polyol, said composition having an interleukin-2 specific activity of at least about 120,000 units/mg of protein, said activity being at least about 40% of the specific activity of purified Jurkat IL-2. The present invention also provides a process for preparing the recombinant human IL-2 wherein human rIL-2 which has been lyophilized after purification by HPLC is mixed with water and, if desired, a polyol to form a suspension and the resulting suspension is heated at a temperature of from about 25° C. to about 95° C. for at least about two hours.

DETAILED DESCRIPTION OF THE INVENTION

The composition of the invention consists essentially of water, rIL-2, and optionally a polyol as a carrier. As used herein the expression "consisting essentially of" means that the composition can contain other ingredients so long as they do not materially alter the basic and novel characteristics of the composition, e.g., its high specific activity.

The rIL-2 is prepared by expression of microorganisms, such as *E. coli*, which have been transformed by a plasmid carrying the rIL-2 gene. Methods of preparing such microorganisms are described in the article by Rosenberg, et al., mentioned earlier herein and by Devos, et al., *Nucleic Acids Research*, 11, 4307–4323 (1983). Preferably, the rIL-2 is prepared by the procedures given in copending U.S. patent application Ser. No. 628,145, filed on July 5, 1984, now abandoned, the pertinent sections of which are incorporated herein by reference, and by using *E. coli* K12 strain HB101. Pursuant to those procedures the *E. coli* is transformed with plasmid pTrpEIL-2, which can be obtained from ATCC deposit bearing accession number 39750, and the resulting transformed *E. coli* is grown at 37° C. in an appropriate medium.

The rIL-2 is recovered from a culture of the transformed microorganism and is purified to substantial homogeneity. The culture is harvested to yield a cell paste from which rIL-2 is extracted. Preferably, the rIL-2 is extracted at about 0° C. to about 25° C. by using an organic acid selected from the group consisting of $C_1$ to $C_5$ carboxylic acids. Most preferably, the carboxylic acid is acetic acid. Suitable concentration of carboxylic acid is from about 60% to about 100% (v/v), preferably from about 60% to about 80% (v/v), most preferably about 80% (v/v). The process of extraction of the rIL-2 is further described in copending application Ser. No. 759,180, filed on July 26, 1985, now U.S. Pat. No. 4,675,389 which is incorporated herein by reference. Suitable ratio of carboxylic acid to cell paste is from at least about 8 mL of acid per gram of wet cell paste. The cell paste and carboxylic acid are mixed together for about 30 minutes or more and then the resulting suspension is centrifuged to provide a supernatant which represents an acidic extract of recombinant protein.

Procedures for purification of protein by chromatography are well known. Preferably, the extracted rIL-2 is purified by HPLC. The acidic extract of rIL-2 can be optionally diluted with 0.1% by volume trifluoroacetic acid solution, filtered through a suitable acid-stable filter, such as a 0.45 μm nylon filter, and then applied to an HPLC system which consists of a column, equilibrating solvent, and eluting solvent. Suitable columns include silicate-based supports derived either with low molecular weight alkyl chains, such as $C_3$ or $C_4$, or with phenyl moieties, both with an average particle size of about 5 to about 300 μm and pore sizes of about 30 nm or greater. A suitable equilibration solvent is a 0.1% aqueous solution of trifluoroacetic acid (TFA) with acetonitrile or propanol in an amount of from about 0 to 15% (v/v). A suitable eluting solvent is a 0.1% aqueous solution of trifluoroacetic with acetonitrile or propanol present in an amount up to and including about 70% (v/v). For rIL-2 the alkyl column will generally be used first and then the phenyl column is used.

The protein in eluting solvent from the HPLC treatment is fast-frozen and lyophilized to dryness. Optionally, the protein containing eluting solvent can be combined with carrier protein or a polyol or a dilute solution of either prior to lyophilization. The use of a dilute solution of polyol facilitates freezing of large volumes of dilute recombinant protein in the HPLC eluting solvent. The concentration of polyol in the dilute solution can be from about 2 mM to about 15 mM and the volume of diluent can be from about 1 volume per volume of HPLC eluting solvent to about 3 volumes. Suitable carrier protein include human, bovine or guinea pig serum albumin. If a carrier protein is employed prior to lyophilization, the quantity used must be insufficient to interfere with the resuspension and heating step which brings about enhanced activity in the process of the invention. If human serum albumin is employed as a carrier protein prior to lyophilization, it is preferably present in a concentration of 2 mg/mg of rIL-2 or less. Preferably, carrier protein is not employed so that a final composition free from carrier derived from blood is obtained. Suitable polyols are as given herein below.

In the process of the invention the lyophilized rIL-2 is resuspended by adding the lyophilized caked of protein to water or optionally a dilute aqueous solution of a polyol and heating the resulting mixture at a temperature of from about 25° C. to about 95° C. for at least about two hours. Preferably, the mixture is heated to a temperature of from about 35° C. to about 75° C. and, most preferably, from about 50° C. to about 60° C. to obtain the highest level of specific activity. Preferably, the concentration of rIL-2 in the mixture is at least about 0.5 mg/mL. In a preferred embodiment of the invention, the suspension of rIL-2 resulting from the heating step is rapidly cooled to about 0° C. The process of the invention provides a rIL-2 composition having substantially increased IL-2 specific activity as compared to rIL-2 prior to treatment by the process.

Preferably, in the process of the invention a polyol is used and, preferably, in the composition of the invention a polyol is present. Polyols suitable for the present invention are in general either water-miscible or water-soluble. The use and presence of the polyol confers the greatest increase in activity of the rIL-2. The polyol is selected from the group consisting of polyhydroxy alcohols, monosaccharides and disaccharides. Suitable polyhydroxy alcohols include mannitol, glycerol and glycols such as ethylene glycol, propylene glycol, and trimethylene glycol but glycerol and ethylene glycol are preferred and glycerol is most preferred. Suitable monosaccharides for use in the process and composition of the invention include glucose, fructose, arabinose and mannose but glucose is preferred. Suitable disaccharides include maltose and sucrose, but sucrose is preferred.

The polyol can be added either during lyophilization or prior to heating or can be added during both steps. The polyol is employed during resuspension in an amount sufficient to make the concentration of polyol in the composition which is to be heated from about 0.03M to about 3.0M. In a preferred embodiment 20 μL of solution having 50 mg of polyol per mL of solution is used for each 1 mL of HPLC purified rIL-2 (0.2 mg rIL-2/mL). The resulting solution is lyophilized to dryness and the material obtained is added to 100 μL of the polyol solution. Most preferably, the polyol is one which is acceptable for use in an injectable composition for treating humans.

It is known that IL-2 has three cysteines, designated A, B and C. Jurkat (natural human) IL-2 has an AB disulfide bridge. A result of expression of a recombinant polypeptide is that virtually all cysteines are reduced. The cysteines can be reoxidized by exposure to air and aging to form random disulfide bridges. In the case of rIL-2, three interchain bridges are possible: AB, BC, and AC. Only the form with the AB disulfide bridge is purported to be biologically active. Although the present invention is not limited by theory, it is believed that the heating step of the present invention enables the rIL-2 molecules to adopt to a substantially greater extent the normal AB disulfide bridge.

The composition of the invention has a specific activity of at least about 120,000 units/mg of protein, preferably at least about 140,000 and, most preferably, from about 170,000 to about 220,000 units/mg of protein. The specific activity of the composition of the invention is at least about 40% that of pure Jurkat (natural human) IL-2 which has a specific activity, as used herein, of about 300,000 units/mg of protein. As used herein, specific activity is measured by the rIL-2 assay described in Gillis, et al., Immunology 120, 2027–2032 (1978), with the following modifications: (a) Dulbecco's Modified Eagle Medium (DMEM)+high glucose medium is used in place of Clicks medium (b) penicillin and N-2-hydroxy-piperazine-N'-2 ethanesulfonic acid (HEPES) buffer were omitted, (c) 0.1M sodium pyruvate is added, and (d) Jurkat (natural human) IL-2 is used as a standard. In the foregoing assay the activity of an IL-2 sample is determined by measuring the concentration-dependent incorporation of $^3$H-thymidine into a cloned IL-2 dependent murine T-lymphocyte line. Comparison of the incorporation induced by an unkown sample to that of a known standard yields the relative activity of the unknown sample.

Pursuant to the above assay and using Jurkat IL-2 which has a specific activity of 300,000 units/mg as a standard, the international standard which should be at least 500 units/ml has an activity of 10.7±2.5 units/ml (n=6). The international standard is a reference sample described in Bertoglio, et al., Lymphokine Res. 1, 121–127 (1982). Hencce, when an IL-2 preparation is assayed using the Jurkat IL-2 standard described herein, the IL-2 preparation will have a activity value which is about one-fiftieth (1/50) of the value which would be obtained when the international standard is employed. Specific activity measurements as given herein have a precision of about ±20%. It is to be understood that the process of the invention can provide a rIL-2 composition of increased specific activity even if the final activity is less than 120,000 units/mg of protein.

IL-2 is thought to be useful in elevating immune responses and restoring immune deficient T cell populations. Bylinsky, Fortune, Nov. 25, 1985, pp 16–21, reports cancer research by S. A. Rosenberg. Rosenberg treated patients with massive doses of interleukin-2 together with the patient's own activated cancer-killing cells. First about 10% of the patient's white blood cells were withdrawn and mixed with IL-2. The cells and large doses of IL-2 were injected back into the patient. According to the report, IL-2 multiplies the killer cells in the patient's body and these cells start attacking the tumor. In his first study, Rosenberg is reported to have obtained remissions in half of 30 critically ill patients.

The invention is further illustrated by the following examples in which all percentages are by volume, all temperatures are in degrees Celsius, and specific activity was measured by the assay previously described herein using Jurkat IL-2 with a specific activity of 300,000 units/mg as a standard unless otherwise stated.

EXAMPLES 1–6

Recombinant IL-2 is prepared by the method described in U.S. patent application Ser. No. 628,145, filed on July 5, 1984 using E. coli K12 strain HB101 transformed with plasmid pTrpIL-2. Cells are grown in 9.9 liters of supplemented M9 medium. Cell paste is harvested by centrifugation and stored frozen at −70°. The paste is thawed and resuspended at 2 mL/g of paste in 0.01M Tris Cl, pH 8.0, 0.001M ethylenediaminetetraacetic acid (EDTA), 0.15M NaCl(TE+NaCl). The cells are disrupted by sonication and centrifuged at 12,000× g for 15 minutes. The resulting supernatant which contains less than 1% of the IL-2 is discarded, and the resulting pellet is resuspended at 12 mL/g of paste in 67% acetic acid. The suspension is stirred at 4° for 1 hour and then centrifuged as described above for 2 hours. The resulting acetic acid supernatant is filtered through a 0.2 μm filter.

The filtered supernatant is subjected to HPLC using a Varex instrument and columns which are 5 cm in diameter by 30 cm high and contain either (a) Vydac $C_4$-derivatized silica (15–20 μm particles, 300 Å pore size) or (b) Vydac diphenyl-derivatized derivatized silica (30 μm particles, 300 Å pore size). As equilibration solvent and eluting solvent are used acetonitrile/water/trifluoroacetic acid (12.5/87.5/0.1) and acetonitrile/water/trifluoroacetic acid (87.5/12.5/0.1). Elution is monitored by UV absorbance of a split stream of eluent.

The filtered acetic acid supernatant is applied to the $C_4$ column at 66 mL/min., washed with equilibrating buffer until baseline absorbance is achieved, and eluted by a two-phase gradient from 12.5% to 50% acetonitrile over 15 minutes and from 50% to 74% acetonitrile over 45 minutes. The eluate containing the rIL-2 is diluted to 15% acetonitrile/0.1% TFA and applied to the diphenyl column at 66 mL/min. The rIL-2 is eluted by a linear gradient from 60% to 80% acetonitrile over 30 minutes. Eluting fractions corresponding to the rIL-2 peak are collected in a baked sterile 1 L stainless steel beaker.

Six 0.5 mL aliquots of the HPLC purified rIL-2 having an rIL-2 concentration of 0.2 mg/mL are taken. To five of these 10 μL of solution of polyol having 50 mg of polyol per mL of solution are added. Next, each of the six rIL-2 mixtures is lyophilized to dryness and the resulting material is resuspended, for each of the five having added polyol, in 100 μL of the polyol solution. The sample having no polyol is resuspended in 100 μL of water. Each resulting suspension is heated at 56° C. for two hours in a plastic tube and then cooled by placing the tube in ice. The specific activity (Sp.A.) of each sample is measured before and after heating. The results are given in Table 1 where specific activity is in units/mg of protein.

TABLE 1

| Example | Polyol | Sp.A. before heating | Sp.A. after heating |
|---|---|---|---|
| 1 | none | 23,200 | 120,000 |
| 2 | glucose | 31,200 | 152,000 |
| 3 | mannitol | 31,600 | 130,500 |
| 4 | sucrose | 39,600 | 132,000 |
| 5 | glycerol | 34,400 | 153,000 |
| 6 | ethylene glycol | 38,000 | 150,000 |

EXAMPLES 7–12 and COMPARISON A

Seven 0.5 mL aliquots of HPLC purified rIL-2 prepared according to a procedure similar to that given in Examples 1–6 are mixed with glucose using a procedure similar to that of Examples 1–6 and then heated for 2 hours at different temperatures. The results are shown in Table 2 where specific activity is in units/mg of protein.

TABLE 2

|  | Temperature | Sp.A. |
| --- | --- | --- |
| Comparison A | 4° | 27,000 |
| Example 7 | 37° | 96,000 |
| Example 8 | 50° | 162,000 |
| Example 9 | 56° | 141,750 |
| Example 10 | 60° | 93,500 |
| Example 11 | 70° | 133,500 |
| Example 12 | 90° | 122,250 |

EXAMPLE 13

Six 100 μL samples of rIL-2 were prepared according to a procedure similar to that given in Examples 1–6 using glucose as the polyol. Each sample was heated at 56° for two hours and then the specific activity was measured in duplicate for each sample. The results gave an average specific activity of 220,000 units/mg of protein.

EXAMPLES 14–17

Twenty 100 μL samples of rIL-2 in water were prepared according to a procedure similar to that of Examples 1–6 except as noted herein. These samples were divided into four sets (Examples 14–17) of five samples each. Within each set one sample was assayed before heat treatment and four were assayed after heat treatment. Example 14 had no polyol added either prior to lyophilization or prior to heat treatment. Example 17 had glucose added prior to both steps. Example 15 had glucose added prior to lyophilization but no additional glucose was added prior to heat treatment. Example 16 had glucose added just prior to heat treatment only. Each sample which was subjected to heat treatment was heated at 56° for about two hours. The specific activity of each sample was measured and the results are given in Table 3 below in units/mg of protein. The values under the "after heating" column are the averages of the four samples for each set. The column designated "lyophil./heat" indicates whether a polyol was added prior to lyophilization and/or just prior to heat treatment and "glu" means glucose.

TABLE 3

|  | lyophil./heat | Sp.A. before heating | Sp.A. after heating |
| --- | --- | --- | --- |
| Example 14 | none/none | 42,000 | 138,000 |
| Example 15 | glu/none | 62,000 | 170,000 |
| Example 16 | none/glu | 36,600 | 141,000 |
| Example 17 | glu/glu | 46,600 | 211,000 |

The invention being claimed is:

1. In a process for preparing a recombinant human interleukin-2 composition consisting essentially of water and recombinant human interleukin-2, the improvement comprising (a) mixing with water to generate a suspension of recombinant human interleukin-2 which has been lyophilized after purification by high performance liquid chromatography, and (b) heating the resulting suspension at a temperature of from about 35° C. to about 95° C. for at least two hours.

2. The process of claim 1 wherein the temperature in step (b) is from about 35° to about 75° C.

3. The process of claim 2 wherein the temperature is from about 50° to about 60° C.

4. The process of claim 3 wherein the recombinant human interleukin-2 is present in the composition in a concentration of at least 0.5 mg/ml.

5. The process of claim 4 wherein a polyol is added in step (a).

6. The process of claim 5 wherein the polyol is selected from the group consisting of polyhydroxy alcohols, monosaccharides, and disaccharides.

7. The process of claim 6 wherein the polyol is present in the composition at a concentration of from about 0.03M to about 3.0M.

8. The process of claim 7 wherein the polyol is a polyhydroxy alcohol.

9. The process of claim 8 wherein the polyhydroxy alcohol is glycerol.

10. The process of claim 6 wherein the polyol is a disaccharide.

11. The process of claim 10 wherein the disaccharide is sucrose.

12. The process of claim 6 wherein the polyol is a monosaccharide.

13. The process of claim 12 wherein the monosaccharide is glucose.

14. the process of claim 7 wherein the polyol is glycerol or glucose, the recombinant human interleukin-2 is prepared by expression of transformed E. coli, and human serum albumin is present in a concentration of 2 mg/mg of recombinant interleukin-2 or less.

15. The process of claim 1 wherein the rIL-2 is lyophilized with a polyol prior to step (a).

16. The process of claim 15 wherein the polyol is selected from the group consisting of polyhydroxy alcohols, monosaccharides and disaccharides.

17. The process of claim 15 wherein an additional polyol is added in step (a).

18. The process of claim 17 wherein each polyol is independently selected from the group consisting of polyhydroxy alcohols, monosaccharides and disaccharides.

* * * * *